(12) United States Patent
Braesel et al.

(10) Patent No.: US 7,040,138 B2
(45) Date of Patent: May 9, 2006

(54) METHOD AND DEVICE FOR THE MONITORING OF GASES

(75) Inventors: Eckhard Braesel, An der Klosterruine 14 a D-17493, Greifswald (DE); Ute Sasum, Greifswald (DE)

(73) Assignee: Eckhard Braesel, Greifswald (DE)

( * ) Notice: Subject to any disclaimer, the term of this patent is extended or adjusted under 35 U.S.C. 154(b) by 45 days.

(21) Appl. No.: 10/275,469

(22) PCT Filed: May 8, 2001

(86) PCT No.: PCT/EP01/05223

§ 371 (c)(1),
(2), (4) Date: May 19, 2003

(87) PCT Pub. No.: WO01/86284

PCT Pub. Date: Nov. 15, 2001

(65) Prior Publication Data

US 2003/0172716 A1    Sep. 18, 2003

(30) Foreign Application Priority Data

May 10, 2000  (DE) ................... 100 22 714

(51) Int. Cl.
*G01N 7/00* (2006.01)
(52) U.S. Cl. ................... 73/19.01
(58) Field of Classification Search ............ 73/19.01, 73/19.05, 19.1, 19.11, 23.2, 23.42
See application file for complete search history.

(56) References Cited

U.S. PATENT DOCUMENTS

| | | | |
|---|---|---|---|
| 3,942,792 A | 3/1976 | Topol | |
| 4,184,359 A * | 1/1980 | Gracey | ................. 73/19.01 |
| 4,236,404 A | 12/1980 | Ketchum et al. | |
| 4,444,040 A | 4/1984 | Sakai et al. | |
| 4,563,892 A * | 1/1986 | D'Aoust | ................. 73/19.05 |
| 4,763,514 A | 8/1988 | Naito et al. | |
| 4,890,478 A * | 1/1990 | Claiborne et al. | ......... 73/19.11 |
| 5,062,292 A * | 11/1991 | Kanba et al. | ............ 73/19.01 |
| 5,400,641 A | 3/1995 | Slemon et al. | |
| 5,659,126 A * | 8/1997 | Farber | ................. 73/19.02 |
| 6,391,096 B1 * | 5/2002 | Waters et al. | ............ 73/23.42 |

FOREIGN PATENT DOCUMENTS

| | | |
|---|---|---|
| DE | 135 158 | 4/1979 |
| DE | 254 827 | 3/1988 |
| DE | 41 36 639 | 5/1993 |
| DE | 198 33 601 | 12/1999 |
| EP | 0 525 933 | 2/1993 |
| EP | 0 534 331 | 3/1993 |

* cited by examiner

*Primary Examiner*—Charles Garber
(74) *Attorney, Agent, or Firm*—Flynn, Thiel, Boutell & Tanis, P.C.

(57) ABSTRACT

The invention relates to method for monitoring dissolved gases in liquid-filled high-voltage installations comprising a sealed separating vessel communicating with a liquid tank, wherein an equilibrium state of the liquid with the gas state prevails in the separating vessel during normal operation and liquid is pumped off from the separating vessel with a pump as to keep the liquid level at a predetermined height, including the following steps; Short-time interruption of the pumping action as to leave the equilibrium state and to increase the pressure in the separating vessel, and withdrawal of a gas sample from the gas phase above the liquid level in the separating vessel for the analysis thereof. The invention moreover relates to a method for monitoring dissolved and undissolved gases, wherein the method for monitoring dissolved gases is performed and undissolved gas is fed back into the separating vessel, and to a device for performing the methods according to the invention.

20 Claims, 2 Drawing Sheets

METHOD AND DEVICE FOR THE MONITORING OF GASES

The invention relates to methods for monitoring gases in liquid-filled high-voltage installations, and to a corresponding device.

High-voltage installations, in particular large scale transformers, are cooled with liquids, mostly with oil. The oil should be monitored so as to allow the detection of malfunctions. An analysis of the occurring gases makes it feasible to find out as to which gas is present in the oil, and in what concentration. In knowledge of the gas present in the oil conclusions can then be drawn to the cause for the formation of the gas. It is, for example, a well-known fact that the occurrence of hydrogen gas in the oil of a transformer is a hint to the occurrence of electric discharges inside the transformer.

A free, undissolved gas in the transformer liquid is, on one hand, a danger for the disruptive strength of the insulating system and, on the other hand, an information carrier for the cause of its formation. If such a free gas is present, a possibly fast analysis of the gas should be possible.

For the optimum monitoring of liquid-filled high-voltage installations the knowledge of the total gas content in the oil, the composition of the dissolved gas, the finding of undissolved gases and/or the composition of the undissolved gases is, therefore, desirable.

EP 0 534 331 A1 describes a device by means of which gases present in oil can be detected by performing a pressure measurement in combination with heat conductivity measurements of the present gas in an isochore equilibrium gas phase. Oil is supplied via a glass filter such that a dynamic pressure is formed. Said method can, therefore, not be used for gas-saturated or gas-oversaturated oils.

A method for the detection of undissolved gases by use of a membrane is described in DE 198 33 601 C1.

It is the object of the present invention to provide an improved method for monitoring dissolved gases in liquid-filled high-voltage installations, which allows an easy gas analysis of the gases dissolved in the oil or, respectively, a method which allows an analysis of the gases dissolved or undissolved in the oil. It is, moreover, an object of the invention to provide a device for the performance of the methods according to the invention.

Said objects are provided by means of a method comprising the features of one of claims 1, 6 or 7 or, respectively, a method comprising the features of claim 8, as well as by means of a device comprising the features of claim 14. Advantageous embodiments are the subject matters of the respective subclaims.

According to the inventive method for monitoring dissolved gases in liquid-filled high-voltage installations a separating vessel is connected with the liquid tank of the high-voltage installation. During normal operation an equilibrium state between the liquid and the gas state is prevailing in the separating vessel. The liquid level is held at a predetermined height by means of a pump, whereby the pump thereby acts underneath the liquid level in the separating vessel.

By briefly interrupting the pumping action or by reducing the pumping performance the liquid level is increased and the equilibrium state is left for a short time. Above the liquid level in the gas phase of the separating vessel the pressure slightly increases until it is above the ambient pressure, so that the withdrawal of a gas sample from the gas phase for the analysis by a sample withdrawal point arranged above the liquid level of the separating vessel is possible.

The expression withdrawal thereby refers to the withdrawal of the gas sample for external analysis purposes as well as to the withdrawal of gas directly supplied to a gas analyzing sensor, "so that a direct online analysis" is feasible.

The invention allows the monitoring of the gases dissolved in the oil in an easy manner. The measurement is simple and can be performed fast and easily, so that it can be performed frequently. On the other hand, measurable changes in the tank oil occur on a long-term basis, normally within an order of magnitude of one day. Insofar a continuous monitoring is guaranteed. The short-time interruptions of the equilibrium gas state when the gas samples are withdrawn are likewise unproblematic due to said different time scales. The withdrawn gas sample then allows an analysis of the oil-dissolved gas in an easy manner, e.g. for monitoring purposes or, respectively, for a malfunction analysis.

The gas sample is withdrawn above the liquid level. The gas can thereby be withdrawn, e.g. manually by means of a septum or a stop valve, or by means of an automatic gas withdrawal cartridge which reacts as of a certain pressure. While a gas withdrawal cartridge ensures an automatic and easy withdrawal, a manual withdrawal can be carried out in a flexible fashion without any additional apparatus. The sample as withdrawn permits a complete analysis of the gas dissolved in the oil. In addition, the composition of the dissolved gases can be determined by means of sensors being free of test gas consumption, e.g. correspondingly modified heat conduction sensors in combination with selective IR sensors. Furthermore, the saturation degree of the gas can be determined with a manometer correspondingly disposed on the separating vessel above the liquid level. Such sensors guarantee additional safety during the analysis of the gas dissolved in the oil and can be used continuously.

Finally, gas can directly be conducted to a sensor by means of a purge-gas line, which is connected with the gas phase of the separating vessel by means of a valve.

The methods according to the invention may be carried out periodically, whereby the method is carried out, the readjustment of the equilibrium in the separating vessel is waited for afterwards so as to carry out the method again. The adjustment of the equilibrium usually only takes a few hours, e.g. two hours, whereas the changes in the tank oil are normally of a longer duration. Accordingly, a continuous monitoring of the tank oil is guaranteed.

By means of sensors free of test gas consumption in the gas phase of the separating vessel above the liquid level the composition of the gases dissolved in the oil can continuously be determined in the equilibrium state, even without having to withdraw a sample. If necessary, the liquid level may thereby be increased by interrupting the pumping action or by reducing the pumping performance for a short time. Thus, more defined and reproducible pressure ratios can be obtained when the measurement is performed.

The methods according to the invention permit an easy monitoring and analysis of the gases dissolved in the oil. The occurrence of additional undissovled gases is reproduced in the withdrawn gas samples or, respectively, in the signals from the sensors. Therefore, a malfunction caused by the occurrence of undissolved gases can be noticed quickly and corresponding arrangements for the elimination thereof can be made.

According to the inventive method for monitoring dissolved and undissolved gases in liquid-filled high-voltage installations, the separating vessel is connected with a ventilation assembly of the liquid tank via an additional feeding pipe, in which a liquid level sensor is disposed in a rising pipe portion. If the same reacts once undissolved gases occur, the above-described method according to the invention is applied for monitoring the dissolved gases. In a subsequent step, undissolved gases are introduced from the liquid tank into the separating vessel, whereby the change in terms of time of the analyzed values and, on the basis thereof, the origin of the undissolved gases is determined.

From precedingly found pragmatical values the reason for the occurrence and the composition of the undissovled gases can be determined on the basis of said temporal change of the analyzed values. Gas samples can be withdrawn therefor. An easy uninterrupted monitoring of the change is feasible, if the signals from sensors free of test gas consumption, which are disposed above the liquid level in the separating vessel, are applied as analysis values.

The procedure according to the invention permits the nearly simultaneous determination of the composition of the dissolved gases in the equilibrium and of the undissolved gases of the oil. By comparing the undissolved gas with the values for the dissolved gas available in the equilibrium state, conclusions can directly be drawn to the composition of the additionally occurred gas. This permits a secure determination of the origin of the additionally occurring undissolved gas. By the nearly simultaneous measurement of the dissolved gases, the composition of the gas dissolved in the oil in the equilibrium state is possible without any interference with the function of the sensor by undissolved gases. The nearly simultaneous measurement moreover ensures that the measurements of the dissolved and the undissolved gases take place under the same further environmental conditions, e.g. the temperature. A safe analysis of the occurring gas is, thus, guaranteed.

According to an advantageous embodiment of the method undissolved gas is, after the performance of a gas withdrawal of the dissolved gas from the equilibrium state, collected in a gas collecting vessel branching off from the feeding pipe into the separating vessel. After the undissolved gas has been admitted into the separating vessel, a gas sample can be withdrawn via the ventilation assembly of said gas collecting vessel, which sample exclusively contains undissolved gas. Thus, an analysis of the undissolved gas in view of its composition is additionally possible.

Undissolved gas occurring in the liquid tank of a high-voltage installation can, for instance, be withdrawn on a gas collection fitting of the liquid tank. The gas collection fitting is thereby advantageously installed in a rising pipe exiting the liquid tank in the upper portion and leading to the separating vessel. Undissolved gas is then withdrawn at the ventilation assembly of the gas collection fitting in the normal state oil is withdrawn from the gas collection fitting. Thus, the gas dissolved in the oil can be analyzed and monitored in the separating vessel by means of the methods as described. If undissolved gases occur, the same are collected in the gas phase of the gas collection fitting and can be withdrawn via the ventilation assembly thereof and supplied to the separating vessel according to the inventive method. If the gas collection fitting is inserted in the rising pipe directly above the liquid tank, a particularly representative monitoring is feasible, as the gas collection fitting is disposed in the direct proximity of the oil in the liquid tank.

If the high-voltage installation is already equipped with a gas collecting relay for the detection of undissolved gases, e.g. a beech wood relay, the undissolved gas can directly be withdrawn for the analysis thereof from said gas collecting relay.

If such an already provided gas collecting relay is used, a retrofitting by an additional gas collection fitting may be avoided.

A device for monitoring gases in liquid-filled high-voltage installations according to the invention comprises a separating vessel and a feeding pipe connected with said separating vessel and the liquid tank of the high-voltage installation, whereby the feeding pipe runs into the separating vessel at a height being above the liquid level in the separating vessel during normal operation. Furthermore, a pump is provided, which acts at a point of the separating vessel underneath the liquid level. The separating vessel comprises at least one withdrawal valve above the liquid level for the withdrawal of gas samples, as well as a height level measuring system for the detection of the height level.

An equilibrium state is formed in the sealed tank of the separating vessel, namely with a liquid level above which gas of the gases dissolved in the oil can be found and underneath of which corresponding liquid is provided. By means of the pump the height level of the liquid level can be regulated, whereby a negative pressure is usually formed in the gas phase above the liquid level. The pump or, respectively, the valve, which can uncouple the pump from the separating vessel, can thereby be controlled by means of a corresponding height level measuring system, whereby the liquid level height serves as controlled magnitude. If a predetermined height level reference point is exceeded, the control circuit switches the pump to participate in the cycle as to decrease the liquid level. If, on the other hand, the liquid level falls underneath a predetermined height level reference point, the pump is uncoupled from the separating vessel as to obtain a rise of the liquid level.

The device according to the invention permits upon the performance of the inventive method for monitoring the dissolved gases by the withdrawal of gas samples on the withdrawal valve above the liquid level the analysis of the gas located in the gas phase. The inventive method for monitoring the dissolved gases can accordingly be performed with the device according to the invention in an easy fashion.

The separating vessel advantageously comprises above the liquid level a feeding pipe with an on-off valve through which the calibration gas for calibrating possibly provided measuring sensors can be fed into the separating vessel. Thus, it is possible to directly draw conclusions to the composition or concentration of the gas by comparing the actual measurements with the calibration measurements.

After a measurement the liquid level can again be lowered by switching on the pump, so that the equilibrium state is readjusted. Above the liquid level gas may, however, also be discharged by a corresponding purge-gas capillary, so as to use said discharged gas for additional analyses with alternative detectors, if necessary.

According to an advantageous embodiment, with which also undissolved gases can be detected, an additional feeding pipe into the separating vessel is provided, which communicates with the liquid tank in the high-voltage installation. In a rising pipe portion of the feeding pipe a liquid level sensor and a valve arrangement are provided for the alternative selection of the first or the second feeding pipe. The liquid level sensor and the second feeding pipe are uncoupled from the separating vessel during normal operation, and the liquid level sensor is surrounded by oil. If undissolved gases are formed in the liquid tank, the oil is ejected from the liquid level sensor with the result that it reacts. In this case the inventive method for monitoring the dissolved and the undissolved gases is performed.

A simple embodiment of this device according to the invention comprises a three-way valve as valve arrangement. A connection is connected to the feeding pipe to the separating vessel, and two additional connections of the three-way valve are connected to the first and the second feeding pipe from the liquid tank.

By means of the second feeding pipe the device according to the invention can be connected to a provided gas collecting relay, e.g. a beech wood relay, of the liquid tank, or, respectively, to the ventilation assembly of a gas collection fitting positioned in a rising pipe from the liquid tank. The first feeding pipe is directly connected with the liquid tank, for instance, on a provided oil withdrawal point, or via the gas collection fitting.

The connection with a gas collection fitting in the rising pipe directly above the liquid tank thereby has the advantage that the proportions are determined directly in the liquid tank, as the gas collection fitting may be arranged in the direct proximity of the liquid tank. A connection to a provided gas collecting relay offers the advantage that no further retrofitting with an additional gas collection fitting is necessary.

According to another advantageous embodiment a separate gas collecting vessel is connected at least to the second feeding pipe, with the gas collecting vessel comprising a connection for the withdrawal of a sample in the upper portion. When undissolved gases occur, said gas collecting vessel can be switched into the cycle so that an independent gas sample withdrawal and analysis of the composition of the undissolved gas is possible.

With reference to the enclosed figure; a preferred embodiment of the device and the method will hereinafter be explained, whereby.

Figure 1:
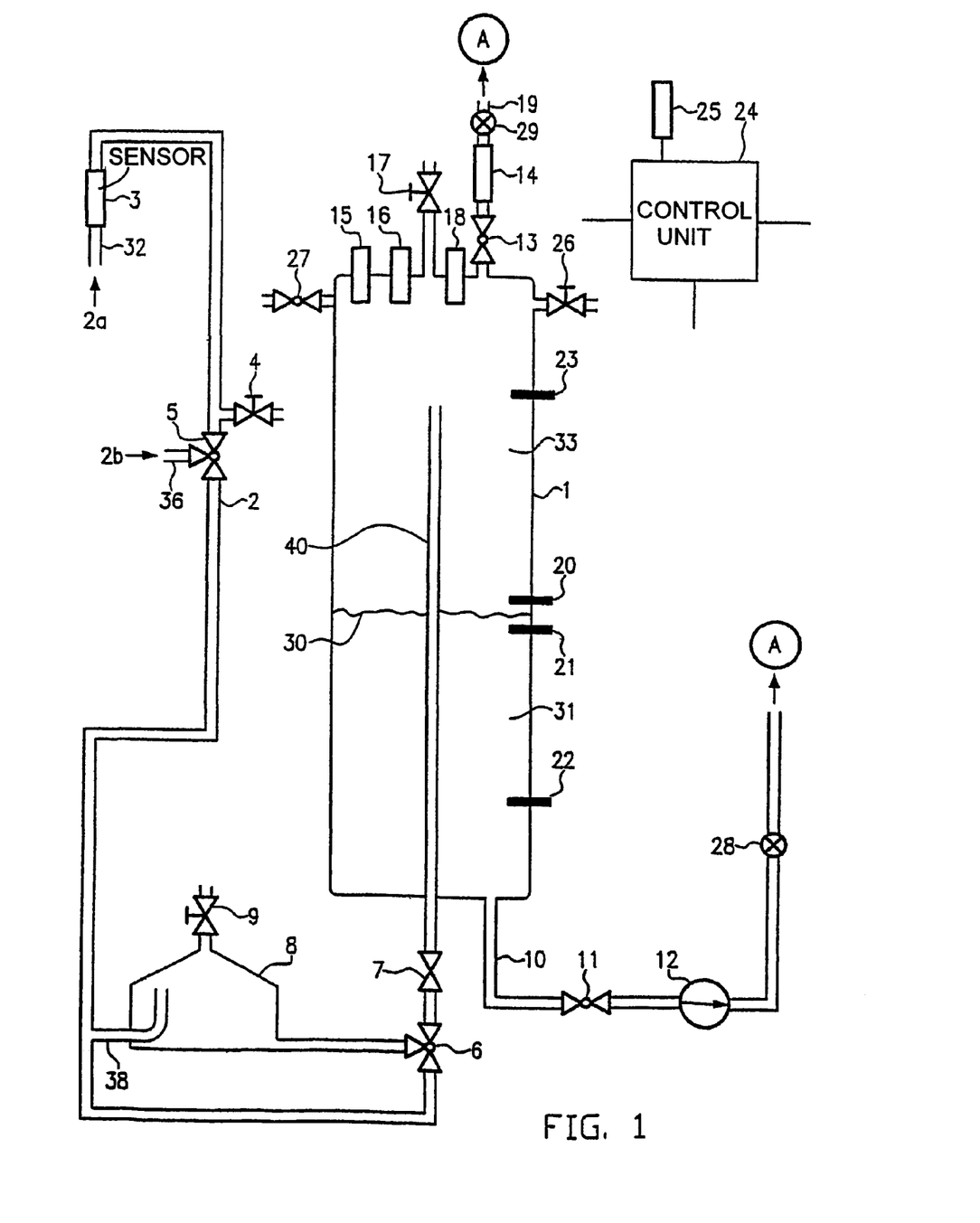
FIG. 1 shows the schematic structure of an embodiment of the device according to the invention, FIG. 2 schematically shows a possible connection variant of the device according to the invention.

The invention is explained on the basis of an air-breathing oil transformer. FIG. 1 shows the measuring device schematically. Connections 2*a* and 2*b* lead to the liquid tank 48 of the air-breathing oil transformer. For example, the winding body of the oil transformer is disposed in the transformer tank 50. Such an oil transformer comprises, in accordance with the prior art, an oil conservator A shown, in the figure, only as a connecting option and arranged higher than the measuring device according to the invention. The oil conservator serves to compensate the volume increase of the oil in the transformer tank 50 in the operating state, which is due to the lost heat conveyed by the winding body. The oil conservator A, also called expander, is an upwardly opened tank exposed to atmospheric pressure, being connected with the tank 50 via the rising pipe 54, in which tank 50 the oil level has to be between an upper and a lower mark. The distance from the base of the transformer tank up to the oil level in the oil conservator usually is 5 m and more. The static column of the oil in the oil conservator is, therefore, proportional to the pressure in the transformer tank 50. The transformer tank has a volume of a few m³ up to about 100 m³. About 3% to 8% of the oil are provided in the oil conservator A. The temperature of the operating oil in the tank is about 35° up to 90° C. The oil in the oil conservator A can partially be fed back to the tank 50 via the rising pipe when, for instance, the oil temperature falls again. During the operation, the oil in the rising pipe between the tank and the oil conservator is subject to convection.

Figure 2:
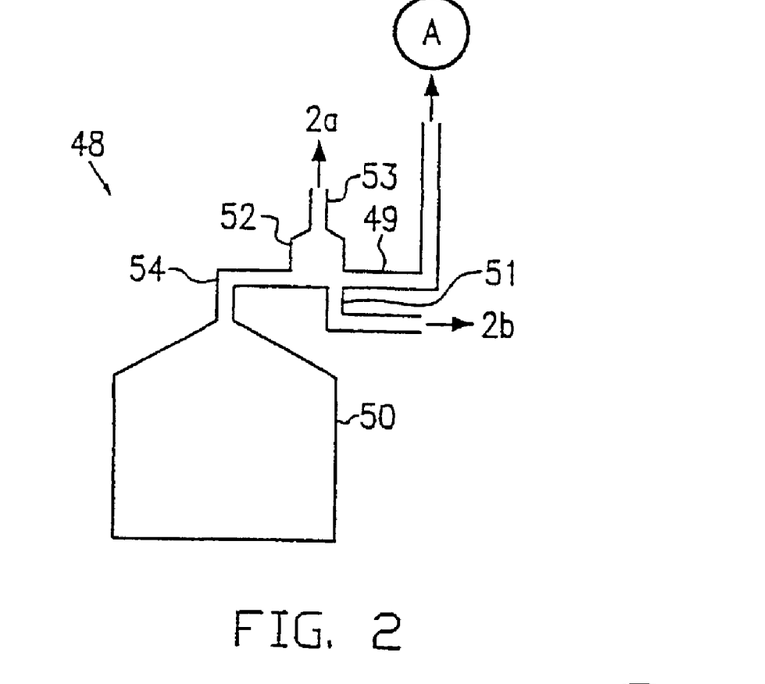

FIG. 2 schematically shows a possible connection variant. A gas collection fitting 52 is integrated in the rising pipe 54, which comes out of the upper portion of the liquid tank 50. The ventilation assembly 53 of the fitting is connected to connection 2*a* of the device illustrated in FIG. 1, while the rising pipe 49 further leads to the oil conservator A of the transformer. The exit 51 of the gas collection fitting 52 leads to connection 2*b* of FIG. 1.

Figure 3:
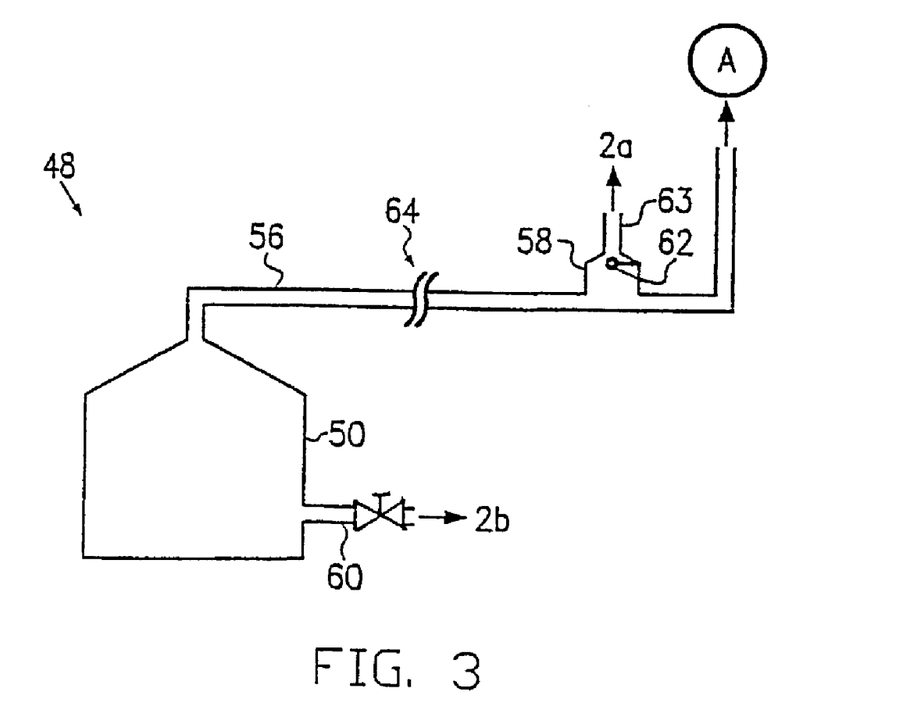
FIG. 3 shows another connection variant of the device according to the invention.

FIG. 3 schematically shows another connection variant. The liquid tank 48 with tank 50 is, according to the prior art, connected with the oil conservator A via a rising pipe 56. A gas collecting relay, e.g. a beech wood relay 58, is located in the rising pipe. The float 62 is outlined inside the relay 58.

The rupture lines 64 suggest that several arches and branches may be provided in the rising pipe 56 and that the beech wood relay 58 does not have to be arranged in the direct proximity of the liquid tank 48. The ventilation assembly 63 of the beech wood relay 58 is connected to connection 2*a* of the device according to FIG. 1. The connection 2*b* of the device according to FIG. 1 is connected with the tank 50, e.g. at an oil sampling point 60 provided on the liquid tank 48.

In both, FIG. 2 and FIG. 3, the components of the liquid-filled transformer required only for the better understanding of the invention have been illustrated.

In the measuring device illustrated in FIG. 1 the feeding pipe 2*b* for feeding the oil is disposed in the separating vessel 1 underneath the beech wood relay shown in FIG. 3 and, respectively, underneath the ventilation assembly 53. The feeding pipe 2*a* serves the feeding of gas undissolved in oil into the separating vessel 1. The separating vessel 1 is preferably arranged in the central or lower portion of the liquid tank 50. Thus, due to the pressure of the oil column resting above the feeding pipes 2*a*, 2*b*, the oil can flow into the separating vessel 1 via feeding pipes 2*a* and 2*b* if the valves are open. As feeding pipe 2*a* is positioned above the ventilation assembly 53 or 63, respectively, undissolved gas, which rises upwardly, can be supplied to the separating vessel via feeding pipe 2*a*.

FIG. 1 shows the substantially cylindrically sealed separating vessel 1 into which a feeding capillary 2 leads from below into the upper portion, which is designated with 33 and which substantially defines the gas phase of the separating vessel and is arranged underneath the oil conservator. During the normal operation a liquid 31 having a liquid level 30 is located in the separating vessel. Feeding pipe 2*b* is connected with a feeding pipe 36 via a three-way valve, with feeding pipe 36 forming the oil supply 2*b* during the operation. At the third way of the three-way valve 5 feeding pipe 32 is connected, in which—as is illustrated—a liquid level sensor 3 is located in a rising pipe portion. As was described above, feeding pipe 32 is connected to the ventilation assembly of the liquid tank or to the exit of a gas collecting relay, which is typically provided in air-breathing oil transformers. Such a gas collecting relay is, for example, a beech wood relay for indicating undissolved gases. Thus, a feeding pipe 2*a* for gas is formed for the measuring device. An exit comprising a stop valve 4 is disposed in feeding pipe 32. Before the feeding pipe 2 runs into the separating vessel 1 it passes a control valve 7. A gas collecting vessel 8 including a ventilation stop valve 9 is disposed in a branching line of feeding pipe 2. The feeding pipe running into said gas collecting vessel 8 is designated by 38. The exit of the gas collecting vessel 8 again runs into the feeding capillary 2 via a three-way valve 6.

Part 40 of the feeding capillary 2 within the separating vessel extends into the upper portion above the liquid level 30.

The separating vessel 1 comprises in its lid a pressure sensor 15, one or more sensors 16 free of test gas consumption, a stop valve 17 as well as a height level sensor 18. The sensor 16 free of test gas consumption is, for instance, a heat conduction sensor modified for the analysis of the dissolved gases in combination with selective IR sensors. The height level sensor 18 is adjusted to a predetermined point of reference 20, 21, 22, 23 of the separating vessel 1. A purge-gas capillary 19 including an on-off valve 13 and a check valve 29 is passed from the lid of the separating vessel 1 into the gas phase of the oil conservator A of the transformer. Alternatively working measuring sensors 14 may be arranged in the purge-gas capillary 19.

A stop valve or, respectively, a septum 26 and an on-off valve 27 are disposed on the top of the separating vessel 1.

A discharge capillary 10 including an on-off valve 11 and a pump 12 is passed from the bottom of the separating vessel 1 into the oil conservator A of the transformer. A check valve 28 is inserted downstream of the pump 12.

All aforementioned sensors, valves and points of reference of the separating vessel 1, as well as the pump 12, are connected with a control and evaluation unit 24, which has been shown only schematically, by means of corresponding lines. The evaluation unit 24 may additionally be equipped with a pressure sensor 25 for measuring the ambient pressure. The evaluation unit 24 can finally be connected to the signal circuit of a gas collecting relay 58, namely in case that connection 2a is connected with such a gas collecting relay, e.g a beech wood relay 58.

The control and evaluation unit 24 has, among others, the function of a closed-loop control circuit. The liquid level height serves as controlled magnitude, which is monitored by the height level sensor 18. If a predetermined point of reference is exceeded, the performance of the pump 12 is increased or, respectively, the valve 11 is opened by the control and evaluation unit 24. If a predetermined height level mark is not reached the pump 12 is switched off or, respectively, the valve 11 is closed so that the liquid level rises again.

The operation of the measuring device according to the invention will hereinafter be explained by means of an example, whereby connection 2a is connected to the ventilation assembly of a beech wood relay 58 and connection 2b to the tank 50 of the oil transformer, as is illustrated in FIG. 3. It is known that beech wood relays have since long been an essential element for monitoring and protecting oil-filled transformers during operation. Undissolved decomposition gases produced by an error in the transformer are collected in the beech wood relay 58, which releases an alarm once a certain gas quantity is exceeded, or causes the transformer to be switched off, if necessary. Both, the signal for releasing an alarm and the signal for switching off the transformer are typically caused mechanically by corresponding floats 62. Other switching mechanisms, e.g. electronic ones, may however also be provided.

The hereinafter exemplarily mentioned time indications and parameters relate to a measuring device which has the following advantageous dimensions. The diameter of the capillaries 2, 10, 19, 32 36 is smaller than or equal to 4 mm. The volume of the separating vessel 1 is about 300 ml, whereby the height of the separating vessel is smaller than or equal to 50 cm. The volume of the gas collecting vessel 8 is about 50 ml. The points of reference 20 and 21 are arranged about centrally in the separating vessel and have a distance of about 3 mm. The temperature of the separating vessel typically is 35° to 90° C. The installation of the measuring device can, for example, take place in the lower or central portion of the tank 50.

The measuring device according to the invention has to be filled prior to the start. In the initial state all valves are closed. Connection 2a is connected to the ventilation assembly of the beech wood relay 58. For ventilation purposes the stop valve 4 is opened for a short time. The three-way valves 5 and 6 are opened in a longitudinal direction, valves 7 and 13 are opened and the height level sensor 18 is connected to participate, all of which may take place either manually or by means of the control and evaluation unit 24. The separating vessel 1 is filled with oil via line 32, 2 up to the point of reference 20. The separating vessel is at first filled via feeding pipe 2a so as to make sure that the feeding pipe 2a, 32, which will then be used as feeding pipe for undissolved gas, is ventilated. The separating vessel could, however, also be filled right away via feeding pipe 2b, 36. The control and evaluation unit 24 thereupon opens valve 11 and switches on the pump 12, which is coupled with the height level sensor 18 in such a manner that the oil level is kept between the points of reference 20 and 21. After an inflow time of, for example, 5 minutes the three-way valve 5 switches to transverse direction. As connection 2b is connected with the tank of the liquid tank of the transformer, tank oil now accordingly flows into the separating vessel 1 via pipe 36, 2. Due to the overpressure in correspondence with the oil column in the oil conservator the oil can flow into the separating vessel 1 via feeding pipes 2a, 2b. The negative pressure produced by the pump 12, moreover, draws in the oil in the feeding pipes. After, for instance, another 10 minutes the three-way valve 6 switches to transverse direction so that the oil flows through the gas collecting vessel 8. The stop valve 9 is opened for a short time for ventilation purposes and is closed again.

In a subsequent step automatic gas withdrawal cartridges are mounted on the stop valves 9 and 17, and the valves are opened. The gas withdrawal cartridges are connected in a conventional manner with the control and evaluation unit 24 via corresponding pipes.

The measuring and evaluating process can now be started. The three-way valve 6 is switched back to longitudinal direction either manually or by the control and evaluation unit 24, and the liquid level sensor 3, the pressure measuring sensor 15, the modified heat conduction sensor 16 in combination with selective IR sensors and the optional additional measuring device 14 are switched on.

The oil flow through the separating vessel 1 depends on the oil level height in the oil conservator A and on the gas saturation degree of the oil. For compensation purposes the control valve 7 has been provided, which is adjusted, for example, to 4 liters per second. The parameters as indicated result in an adjustment time for the equilibrium pressure in the gas phase of the separating vessel 1 of about 2 hours, whereby said adjustment time depends, among others, on the design of the feeding capillary 2. During the adjustment of the equilibrium pressure oil flows continuously to the separating vessel via feeding pipes 2b, 36 and is pumped off by the pump 12 so as to keep the liquid level between the reference points 21 and 20. The pumped off oil is then fed back to the oil conservator and, thus, back to the tank 50, so that a closed cycle is formed.

Upon the adjustment of the equilibrium pressure the signals of the pressure measuring sensor 15 and of sensor 16 no longer change. The gas from liquid 31 is in the gas phase 33 of the separating vessel 1, whereby the gas phase contents are determined according to Henry Dalton's law of partial pressures. The signals from the pressure measuring sensor 15 and from sensor 16 in combination with selective IR sensors can directly be used for the analysis of the gas. Thus, the gas saturation degree can be determined from the pressure values and, with a correspondingly modified heat conduction sensor 16 in combination with selective IR sensors, the composition of the dissolved gases in the oil can be determined and/or continuously be monitored.

Different processes can now be performed. The calibration will be described first. The control and evaluation unit 24 closes the on-off valve 11 and switches off the pump 12. The oil level thereupon 30 rises up to the point of reference 23. It the same is reached, the on-off valve 27 is opened automatically by the control and evaluation unit 24, or manually, and calibration gas is flushed in. The on-off valve 13 is thereby opened, so that no additional overpressure is produced. The composition and the pressure of the calibration gas are known, so that calibration values can be defined from the signals of the pressure sensor 15 and the heat conduction sensor 16. The on-off valve 13 can now be closed again.

After the calibration is finished, the on-off valve is opened again manually or by the control and evaluation unit 24, and the pump 12 is started so that the oil level again reaches the control range of the point of reference 20 or 21, respectively.

The withdrawal of the gas sample takes place as follows. At first, the equilibrium pressure value of sensor 15 is stored. Pump 12 is switched off and the on-off valve 11 is closed. After switching off the pump the oil level in the separating vessel 1 rises. When reaching the point of reference 23 a sufficient pressure, e.g. of $1.2 \cdot 10^5$ Pa, has been reached, so that a gas sample can be withdrawn via the stop valve or, respectively, via the septum 26. Alternatively, an automatic gas withdrawal into the screwed open gas withdrawal cartridge may be performed via stop valve 17. The withdrawn gas can be analyzed and delivers information on the share, the concentration and the composition of the gas dissolved in the oil.

Finally, if required, other analyses can be carried through with additional other measuring sensors 14. For this purpose, other than with the above-described withdrawal method, the gas sample is not withdrawn on the stop valve 26 or stop valve 17, but valve 13 is opened when a sufficient pressure in the separating vessel 1 has been reached, and is closed again after the measurement with the sensor 14.

After the sample has been withdrawn, the on-off valve 11 is opened again by the control and evaluation unit 24, or manually, and pump 12 is started so that the oil level reaches the control range of the points of reference 20, 21.

As measurable changes in the oil of the liquid tank of the transformer occur on a long-term basis, i.e. larger than or equal to a day on a time scale, the gases dissolved in the oil can more or less continuously be monitored with the aid of the measuring device, if the measurement is performed once or several times a day. Due to the large time scale it is also unproblematic that the equilibrium state is disturbed for a short time.

If a permanent monitoring is to be carried out, the withdrawal is performed periodically, whereby, after the performance of a measurement, one has to wait until the equilibrium state has readjusted itself, i.e. about 1 to 2 hours.

The device therefore permits, if required, a continuous measurement of the gas saturation degree by the pressure measuring sensor 15, information on the composition of the gas by the modified heat conductivity sensor 16 in combination with selective IR sensors, and a complete analysis of the dissolved gas by means of the withdrawn gas samples.

The course of the procedure in the case of additionally occurring undissolved gases will be explained in the following.

During the normal operation the three-way valve 5 is switched on to connect connections 36 and 2. Valve 4 is closed. As was described, 2a is in this embodiment connected to the gas collecting phase of beech wood relay 58. Undissolved gas, which was collected in said gas phase, expels oil from the feeding pipe 32 so that the liquid level sensor 3 reacts and supplies a signal to the evaluation and control unit 24.

When the liquid level sensor 3 reacts, the comparative state for dissolved gases is controlled or, respectively, generated in the separating vessel 1 by means of the control and evaluation unit 24. If the valve 11 has not been operated, for example, for a longer period of time, e.g. for 2 hours, an equilibrium state in the separating vessel 1 can be assumed, as no calibration or withdrawal processes have taken place. If, however, the equilibrium state had been disturbed by a withdrawal within a period of time of about 2 hours, the equilibrium pressure in the separating vessel 1 has typically not yet been readjusted. The evaluation and control unit 24 then forms the quotient from the currently measured pressure value of sensor 15 and the pressure value stored prior to the last calibration or withdrawal. With the so formed thinning factor a dimension for the deviation from the equilibrium state is known. On the basis of said thinning factor the measured values of the sensors will be corrected.

Only if a calibration gas supply for calibrating valve 27 has taken place shortly before the liquid level sensor 3 reacted, the ongoing performance can take place only after 1 to 2 hours when the calibration gas has evaporated from the separating vessel 1 to a sufficient extent.

After the liquid level sensor 3 reacts, the control and evaluation unit controls for safety reasons as to whether the liquid level 30 is between the points of reference 20 and 21. Prior to the continuance of the process one has, if necessary, to wait until the liquid level 30 is back between the points of reference 20 and 21, namely through pumping by pump 12.

If the liquid level sensor 3 reacts, at least a smaller concentration of undissolved gases is present. If, in addition, a gas collecting relay reacts, e.g. the beech wood relay 58 of the oil transformer, higher concentrations of undissolved gas are present, so that the following procedure advantageously takes place. The three-way valve 5 remains, at first, in the position in which it connects the liquid tank in the oil transformer to separating vessel 1 via pipes 36 and 2 and closes pipe 32. Thus, a sample of the dissolved gas can be withdrawn in accordance with the above description.

After the oil level has again reached the control range between reference points 20 and 21, the three-way valve 5 switches to longitudinal direction and connects the feeding pipe 32 with the feeding capillary 2. The three-way valve 6 switches to transverse direction, so that the gas collecting vessel 8 is likewise connected. As undissolved gases are provided in the feeding pipe 32, the same are now transported through the feeding capillary 2 into the gas collecting vessel 8 first and then into the separating vessel 1, whereby the time functions of sensors 15 and 16 change. The origin of the undissolved gases can be derived from the change in said time functions. Because the undissolved gases flow into separating vessel 1, the liquid level 30 falls. If the oil level reaches the bottom point of reference 22, valve 11 closes and the pump 12 is switched off. Valve 13 is now opened and the undissolved gas, which has been transported into the separating vessel 1, escapes via the purge-gas capillary 19. If no signal applies to the liquid level sensor 3 any longer, the undissolved gas has been driven out of the liquid tank of the transformer via feeding pipes 32 and 2, i.e. liquid is again provided on the liquid level sensor 3. The automatic gas withdrawal cartridge above the gas collecting relay 8 on the stop valve 9 is now released by the control and evaluation unit 24, or manually. Undissolved gas has accumulated in the gas collecting vessel 8, so that undissolved gas is collected in the gas withdrawal cartridge on the stop valve 9.

As the purge-gas capillary 19, which is connected with the oil conservator, is opened, the oil level rises again in the separating vessel 1. For best possibly removing the undissolved gases from the separating vessel 1, the control and evaluation unit 24 causes the oil level 30 to rise up to the point of reference 23. The three-way valve 5 is thereupon again switched to transverse direction, so that the liquid again passes from tank 50 of the oil transformer via feeding pipe 36, 2 into the separating vessel 1. The three-way valve 6 again switches to longitudinal direction, so that a flow through the gas collecting vessel 8 no longer takes place. By switching on the pump 12 and opening the valve 11 and by simultaneously closing valve 13 it is achieved that the oil level 30 again reaches the control range between the points of reference 20 and 21. Upon the expiration of a certain time, e.g. 2 hours, the equilibrium state in the separating vessel 1 is readjusted.

Stop valves 9 and 17 are closed manually or by the control and evaluation unit 24, and the automatic gas withdrawal cartridges, which were fastened thereon, are removed. The gas contained therein is now ready for gas-chromatographic complete analyses. For adjusting the normal state, the gas collecting vessel 8 must still be ventilated via stop valve 9.

In view of the gas-chromatographic complete analyses it is thereby a particular advantage that the equilibrium gas withdrawn on the gas withdrawal cartridge 17 was withdrawn nearly simultaneously with the undissolved gas withdrawn on stop valve 19. Laborious conversions due to a temporal delay between the withdrawal of the equilibrium gas and the undissolved gas are accordingly not necessary.

Described was the case that the liquid level sensor 3 reacts and that, in addition, undissolved gases are indicated by means of the beech wood relay 58 provided on the transformer. It may, however, also be the case that the liquid level sensor 3 reacts without any simultaneous signaling by the beech wood relay. In this case only very small amounts of undissolved gases are present, and a deviating process is carried out. By switching the valve 5 to longitudinal direction the feeding pipes 32 and 2 are connected with each other so that the undissolved gases enter into the gas phase 33 of the separating vessel 1. Thus, the time functions of the sensors 15 and 16 are changed and, as was described, the determination of the origin of the undissolved gas is applied. By means of said alternative procedure at least the origin of undissolved gases can be detected, even though the concentrations thereof are small.

Thus, it is possible with, the device according to the invention to monitor more or less continuously the equilibrium state of the gases dissolved in the oil. For this purpose, manipulating devices, e.g. the withdrawal device 26 or 17 are provided. The sealed separating vessel 1 forms an equilibrium gas phase, which still contains an equilibrium gas when already undissolved gases apply to connection 2*a*. Thus, it is possible that the parameters of the equilibrium gas and the parameters of the undissolved gases are determined nearly simultaneously. As the equilibrium parameters of the gases dissolved in the oil had already been determined before the undissolved gases were introduced into the gas phase of the separating vessel 1, an interference with the sensor function by the undissolved gases allowed to flow in subsequently are insignificant.

The measuring device for liquid-filled high-voltage devices can be connected to present sampling points for liquids and undissolved gases. An equilibrium gas phase for the dissolved gases is continuously provided, in which sensors free of test gas consumption can work and which can periodically be pressure-changed by means of the liquid level for calibrations, gas withdrawals or elutriations for supplemental sensor measurements. The supply of occurring undissolved gases can take place directly and fast after the appearance thereof, and they can be subjected to an external complete analysis by means of separate automatic gas withdrawal cartridges. For this purpose a sample of the equilibrium gas withdrawn nearly simultaneously may serve as reference.

The invention claimed is:

1. Method for monitoring dissolved gases in liquid-filled high-voltage installations comprising a sealed separating vessel communicating via a first feeding pipe with a liquid tank of the high-voltage installation, wherein the liquid tank is connected with an oil conservator via a pipe, including the following steps:
   a) filling the separating vessel via the feeding pipe with the liquid from the liquid tank, wherein, due to the static column of the liquid above the feeding pipe, the liquid can flow from the liquid tank into the separating vessel,
   b) maintaining an equilibrium state between the liquid and the gas phase in the separating vessel by keeping the liquid level at a predetermined height through pumping off the liquid with a pump, wherein the pumped off liquid is fed back to the liquid tank or to the oil conservator,
   c) short-term leaving the equilibrium state by interrupting the pumping action or by reducing the pumping performance so as to increase the liquid level in the separating vessel,
   d) analyzing the gas above the liquid level in the separating vessel by
      $d_1$) withdrawing a gas sample of the gas from above the liquid level and/or by
      $d_2$) a sensor free of test gas consumption in the gas phase of the separating vessel above the liquid level,
   e) feeding undissolved gases via a second feeding pipe into the gas phase above the liquid level in the separating vessel,
   f) monitoring the temporal change of the analyzed values, and
   g) evaluating the temporal change of the analyzed values for determining the origin of the undissolved gas wherein undissolved gases are discharged into a gas collecting vessel via a gas pipe branching off from the feeding pipe, and a gas sample is withdrawn from the gas collecting vessel after step b.

2. Method according to claim 1, wherein in step $d_1$ the gas sample is withdrawn manually on a septum or stop valve.

3. Method according to claim 1, wherein in step $d_1$ the gas sample is withdrawn automatically by a gas withdrawal cartridge.

4. Method according to claim 1, wherein in step $d_1$ the gas sample is withdrawn via a valve communicating with at least one sensor for the gas analysis.

5. Method according to claim 1, wherein steps c and d are periodically repeated.

6. Method according to claim 1, wherein the analyzed values comprise results of analyses of one or more withdrawn gas samples.

7. Method according to claim 1, wherein the analyzed values comprise the signals from the at least one sensor free of gas test consumption in the separating vessel above the liquid level.

8. Method for monitoring dissolved gases in liquid-filled high-voltage installations comprising a sealed separating vessel communicating via a first feeding pipe with a liquid tank of the high-voltage installation, wherein the liquid tank is connected with an oil conservator via a pipe, including the following steps:
   a) filling the separating vessel via the feeding pipe with the liquid from the liquid tank, wherein, due to the static column of the liquid above the feeding pipe, the liquid can flow from the liquid tank into the separating vessel,
   b) maintaining an equilibrium state between the liquid and the gas phase in the separating vessel by keeping the liquid level at a predetermined height through pumping off the liquid with a pump, wherein the pumped off liquid is fed back to the liquid tank or to the oil conservator,
   c) short-term leaving the equilibrium state by interrupting the pumping action or by reducing the pumping performance so as to increase the liquid level in the separating vessel,
   d) analyzing the gas above the liquid level in the separating vessel by
      $d_1$) withdrawing a gas sample of the gas from above the liquid level and/or by
      $d_2$) a sensor free of test gas consumption in the gas phase of the separating vessel above the liquid level,
   e) feeding undissolved gases via a second feeding pipe into the gas phase above the liquid level in the separating vessel,
   f) monitoring the temporal change of the analyzed values, and
   g) evaluating the temporal change of the analyzed values for determining the origin of the undissolved gas,
   wherein the undissolved gas is fed from a ventilation assembly of a gas collection fitting arranged directly above the liquid tank in a rising pipe portion between an upper portion of the liquid tank and the separating vessel and connected with the first feeding pipe for the supply of oil.

9. Method for monitoring dissolved gases in liquid-filled high-voltage installations comprising a sealed separating vessel communicating via a first feeding pipe with a liquid tank of the high-voltage installation, wherein the liquid tank is connected with an oil conservator via a pipe, including the following steps:
   a) filling the separating vessel via the feeding pipe with the liquid from the liquid tank, wherein, due to the static column of the liquid above the feeding pipe, the liquid can flow from the liquid tank into the separating vessel,
   b) maintaining an equilibrium state between the liquid and the gas phase in the separating vessel by keeping the liquid level at a predetermined height through pumping off the liquid with a pump, wherein the pumped off liquid is fed back to the liquid tank or to the oil conservator,
   c) short-term leaving the equilibrium state by interrupting the pumping action or by reducing the pumping performance so as to increase the liquid level in the separating vessel,
   d) analyzing the gas above the liquid level in the separating vessel by
      $d_1$) withdrawing a gas sample of the gas from above the liquid level and/or by
      $d_2$) a sensor free of test gas consumption in the gas phase of the separating vessel above the liquid level,
   e) feeding undissolved gases via a second feeding pipe into the gas phase above the liquid level in the separating vessel,
   f) monitoring the temporal change of the analyzed values, and
   g) evaluating the temporal change of the analyzed values for determining the origin of the undissolved gas,
   wherein the undissolved gas is withdrawn from a gas collecting relay of the liquid tank of the high-voltage installation.

10. Device for monitoring dissolved gases in liquid-filled high-voltage installations comprising:
    a sealed separating vessel,
    a first feeding pipe for feeding liquid from a liquid tank into the separating vessel, the first feeding pipe communicates with the liquid tank of the high-voltage installation at a height above a liquid level in the separating vessel when an equilibrium state is prevailing therein, wherein the liquid tank is connected via a conservator connecting pipe with an oil conservator and, due to the static column of the liquid above the first feeding pipe, the liquid can flow out of the liquid tank into the separating vessel,
    a pump connected with the separating vessel at a point underneath the liquid level in the separating vessel,
    a pump connecting pipe for feeding the pumped off liquid from the separating vessel back into the liquid tank or the oil conservator,
    at least one withdrawal valve for withdrawing gas samples located above the liquid level in the separating vessel, and
    a height level measuring system for detecting the liquid level in the separating vessel,
    wherein the height level measuring system is connected with the pump and/or a valve for uncoupling the pump from the separating vessel in a control-circuit-type arrangement such that the pump and/or the valve are controllable in response to the liquid level in the separating vessel, so that a predetermined liquid level height is observed.

11. Device according to claim 10, comprising at least one gas sensor free of test gas consumption in the separating vessel above the liquid level in the equilibrium state.

12. Device according to claim 10, comprising a pressure measuring sensor.

13. Device according to claim 10, comprising a purge-gas pipe for discharging gas out of the separating vessel.

14. Device for monitoring dissolved gases in liquid-filled high-voltage installations, comprising:
    a sealed separating vessel,
    a feeding pipe for feeding the liquid from a liquid tank into the separating vessel, which communicates with the liquid tank of the high-voltage installation and runs into the separating vessel at a height being above the liquid level in the separating vessel when an equilibrium state is prevailing therein, wherein the liquid tank is connected via a pipe with an oil conservator and, due to the static column of the liquid above the feeding pipe, the liquid can flow out of the liquid tank into the separating vessel, a pump connected with the separating vessel at a point underneath the liquid level in the separating vessel, a pipe for feeding the pumped off liquid from the separating vessel back into the liquid tank or the oil conservator, at least one withdrawal valve for withdrawing gas samples and located above the liquid level in the separating vessel, a height level measuring system for detecting the liquid level in the separating vessel, and an on-off valve on the separating vessel above the liquid level for the feeding of calibration gas, wherein the feeding pipe is introduced into the separating vessel from underneath and extends above the liquid level when an equilibrium state prevails in the separating vessel.

15. Device for monitoring dissolved gases in liquid-filled high-voltage installations comprising:

a sealed separating vessel, a first feeding pipe for feeding liquid from a liquid tank into the separating vessel, the first feeding pipe communicates with the liquid tank of the high-voltage installation at a height above a liquid level in the separating vessel when an equilibrium state is prevailing therein, wherein the liquid tank is connected via a conservator connecting pipe with an oil conservator and, due to the static column of the liquid above the first feeding pipe, the liquid can flow out of the liquid tank into the separating vessel, a pump connected with the separating vessel at a point underneath the liquid level in the separating vessel, a pump connecting pipe for feeding the pumped off liquid from the separating vessel back into the liquid tank of the oil conservator, at least one withdrawal valve for withdrawing gas samples located above the liquid level in the separating vessel, a height level measuring system for detecting the liquid level in the separating vessel, a purge-gas pipe for discharging gas out of the separating vessel, and a sensor in the purge-gas pipe for gas analysis.

16. Device for monitoring dissolved gases in liquid-filled high-voltage installations comprising:

a sealed separating vessel, a first feeding pipe for feeding liquid from a liquid tank into the separating vessel, the first feeding pipe communicates with the liquid tank of the high-voltage installation at a height above a liquid level in the separating vessel when an equilibrium state is prevailing therein, wherein the liquid tank is connected via a conservator connecting pipe with an oil conservator and, due to the static column of the liquid above the first feeding pipe, the liquid can flow out of the liquid tank into the separating vessel, a pump connected with the separating vessel at a point underneath the liquid level in the separating vessel, a pump connecting pipe for feeding the pumped off liquid from the separating vessel back into the liquid tank or the oil conservator, at least one withdrawal valve for withdrawing gas samples located above the liquid level in the separating vessel, a height level measuring system for detecting the liquid level in the separating vessel, a second feeding pipe for feeding undissolved gases connecting the separating vessel with the liquid tank and comprising a liquid level sensor in a rising pipe portion, and a valve arrangement for alternatively selecting the first or the second feeding pipe.

17. Device according to claim 16, wherein the valve arrangement comprises a three-way valve whereof the one connection is connected with a rising capillary to the separating vessel and whereof the second or third connection is connected with the first or second feeding pipe.

18. Device according to claim 16, wherein the second feeding pipe connects with a ventilation assembly of a gas collecting relay of the liquid tank of the high-voltage installation and the first feeding pipe connects with the tank of the high-voltage installation.

19. Device according to claim 16, comprising a gas collection fitting whereof a ventilation assembly is connected with the second feeding pipe, wherein the gas collection fitting is arranged in a rising pipe that connects the upper portion of the liquid tank with the first feeding pipe, directly above the liquid tank.

20. Device according to claim 16, comprising a gas collecting vessel into which leads a branch of the second feeding pipe, with a connection in the upper portion for the withdrawal of the sample.

* * * * *